US008599381B2

(12) United States Patent
Statz et al.

(10) Patent No.: US 8,599,381 B2
(45) Date of Patent: Dec. 3, 2013

(54) GAS DETECTOR FOR ATMOSPHERIC SPECIES DETECTION

(75) Inventors: Eric R. Statz, Somerville, MA (US); Alan E. DeCew, Jr., West Newton, MA (US); Jonathan B. Ashcom, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 129 days.

(21) Appl. No.: 13/226,809

(22) Filed: Sep. 7, 2011

(65) Prior Publication Data

US 2012/0182555 A1    Jul. 19, 2012

Related U.S. Application Data

(60) Provisional application No. 61/461,504, filed on Jan. 19, 2011.

(51) Int. Cl.
*G01N 21/00* (2006.01)
*G01N 21/39* (2006.01)

(52) U.S. Cl.
CPC ..................... *G01N 21/39* (2013.01)
USPC ........................... 356/436; 356/437

(58) Field of Classification Search
CPC ............... G01N 21/00; G01N 21/39
USPC .................................. 356/432–444
See application file for complete search history.

(56) References Cited

U.S. PATENT DOCUMENTS 3,843,258 A    10/1974 Shupe
3,939,348 A    2/1976 Barrett (Continued)

FOREIGN PATENT DOCUMENTS

EP    1 150 106 A1    10/2001
EP    1 602 902 A1    12/2005

(Continued)

OTHER PUBLICATIONS

Piironen, P. and Eloranta, E.W., "Demonstration of a high-spectral-resolution lidar based on an iodine absorption filter," *Optics Letters*, 19(3):234-236 (1994).

(Continued)

*Primary Examiner* — Michael P Stafira
(74) *Attorney, Agent, or Firm* — Hamilton, Brook, Smith & Reynolds, P.C.

(57) ABSTRACT

A gas detector includes a receiver configured to receive light from a light source through gas, the light source having a bandwidth on the order of an absorption linewidth of the gas, the receiver including at least a first etalon having a transmission bandwidth on the order of the absorption linewidth of the gas, the transmission bandwidth of the first etalon being substantially smaller than the bandwidth of the light source. The gas detector further includes a first detector for detecting light transmitted through the first etalon, a second detector for detecting light reflected from the first etalon, and a processor that determines the quantity of gas based on the detected transmitted and reflected light. The gas detector can further include a second etalon with a transmission bandwidth approximately equal and adjacent to the transmission bandwidth of the first etalon. Alternatively, the gas detector can include a beam separator that separates the light from the light source into a first beam and a second beam, with a small deflection angle between the first beam and the second beam, thereby modifying the effective thickness of a single optical element for each beam and forming the first and second etalon in the optical element.

39 Claims, 17 Drawing Sheets

(56) References Cited

U.S. PATENT DOCUMENTS

| | | |
|---|---|---|
| 4,076,422 A | 2/1978 | Kohno |
| 4,525,067 A | 6/1985 | Hernandez |
| 5,076,699 A | 12/1991 | Ryan et al. |
| 5,128,798 A | 7/1992 | Bowen et al. |
| 5,243,614 A | 9/1993 | Wakata et al. |
| 5,357,336 A | 10/1994 | Ruhl, Jr. et al. |
| 35,355 A | 10/1996 | Ryan et al. |
| 35,366 A | 10/1996 | Hall |
| 5,606,419 A | 2/1997 | Foosnaes et al. |
| 5,886,247 A | 3/1999 | Rabbett |
| 6,243,170 B1 | 6/2001 | Ershov |
| 6,320,663 B1 | 11/2001 | Ershov |
| 6,359,693 B2 | 3/2002 | Smith et al. |
| 6,539,046 B2 | 3/2003 | Newman et al. |
| 6,750,453 B1 | 6/2004 | Nelson et al. |
| 7,030,991 B1 | 4/2006 | Kampe et al. |
| 7,050,215 B1 | 5/2006 | Johnson et al. |
| 7,301,148 B2 | 11/2007 | Johnson |
| 7,317,536 B2 | 1/2008 | Rafac |
| 7,375,814 B2 | 5/2008 | Reichardt et al. |
| 7,423,751 B2 * | 9/2008 | Hairston et al. ............. 356/318 |
| 7,705,313 B1 | 4/2010 | Russell |
| 8,379,210 B2 * | 2/2013 | Thomson ..................... 356/440 |
| 2004/0000643 A1 | 1/2004 | Karlsson et al. |
| 2004/0223158 A1 * | 11/2004 | Lundqvist et al. ........... 356/432 |
| 2004/0263861 A1 | 12/2004 | Rafac |
| 2005/0046852 A1 * | 3/2005 | Larking et al. ............... 356/437 |
| 2007/0024853 A1 * | 2/2007 | Killinger ...................... 356/437 |
| 2009/0303486 A1 * | 12/2009 | Magari et al. ................ 356/437 |

FOREIGN PATENT DOCUMENTS

| | | |
|---|---|---|
| EP | 2 169 384 A1 | 3/2010 |
| WO | WO 94/11713 A1 | 5/1994 |

OTHER PUBLICATIONS

Kim, D., et al., "A newly designed single etalon double edge Doppler wind lidar receiving optical system," *Review of Scientific Instruments*, 79, 123111 (2008).

Tepley, C.A., "The Doppler Rayleigh Lidar System at Arecibo," *IEEE Transactions on Geoscience and Remote Sensing*, 31(1):36-47 (Jan. 1993).

Irgang, T.D., et al., "Two-channel direct-detection Doppler lidar employing a charge-coupled device as a detector," *Applied Optics*, 41(6):1145-1155 (2002).

Shen, F., et al., "Low Tropospheric Wind Measurement with Mie Doppler Lidar," *Optical Review*, 15(4):204-209 (2008).

Sun, D., et al., "Accuracy Analysis of the Fabry-Perot Etalon Based Doppler Wind Lidar," *Optical Review*, 12(5):409-414 (2005).

International Search Report and The Written Opinion of the International Searching Authority, or the Declaration; International Application No. PCT/US2012/021658; Date of Mailing May 24, 2012.

Notification Concerning Transmittal of International Preliminary Report on Patentability for PCT/US2012/021658, "Gas Detector for Atmospheric Species Detection", mailed on Aug. 1, 2013.

* cited by examiner

GAS DETECTOR FOR ATMOSPHERIC SPECIES DETECTION

RELATED APPLICATION

This application claims the benefit of U.S. Provisional Application No. 61/461,504, filed on Jan. 19, 2011. The entire teachings of the above application are incorporated herein by reference.

GOVERNMENT SUPPORT

This invention was made with government support under FA8721-05-C-0002 awarded by the Air Force. The government has certain rights in the invention.

BACKGROUND OF THE INVENTION

Measuring the concentration of a target gas within the atmosphere at long ranges requires a highly precise, quantitative spectrometer. A low noise detector and method are also needed in order to detect extremely low concentrations. The problem becomes even more challenging when coupled with the effects of atmospheric scintillation and the complicated absorption spectrum of the atmosphere.

One approach to quantitative measurements of trace gases in the atmosphere is pulsed differential absorption lidar (DIAL). In this method, a laser source with a narrow linewidth first produces a pulse tuned on-resonance with a particular gas absorption, then a second pulse tuned slightly off-resonance, and the atmospheric transmission of the two successive pulses is compared. Neglecting the effect of the change in atmospheric absorption over the change in frequency, the ratio of the two pulse intensities corresponds to absorption by the trace gas of interest, because the static atmospheric absorption drops out of the ratio. Beer's law then allows the calculation of a concentration between the source and detector.

Unfortunately, this simple picture is complicated by the technical requirements placed on the laser transmitter (i.e., source). Nominally, the laser must have sufficient power to overcome the average atmospheric absorption in the operating wavelength range (about 0.2-2 dB/km, typically), be as narrow-band as possible to maximize sensitivity to the trace gas, have a stable frequency to reduce the effects of atmospheric slope, and have a high repetition rate providing the benefits of averaging. These are aggressive requirements to meet in a single laser system.

Therefore, there is a need for a gas detector that reduces or eliminates the above mentioned transmitter requirements.

SUMMARY OF THE INVENTION

There is provided a gas detector that generally is designed to be a self-referencing receiver. The gas detector includes a receiver configured to receive light from a light source through gas, the light source having an optical bandwidth on the order of an absorption linewidth of the gas, the receiver including at least a first etalon having a transmission bandwidth on the order of the absorption linewidth of the gas, the transmission bandwidth of the first etalon being substantially smaller than the bandwidth of the light source. The gas detector further includes a first detector for detecting light transmitted through the first etalon, a second detector for detecting light reflected from the first etalon, and a processor that determines the quantity of gas based on the detected transmitted and reflected light.

The processor can calculate the ratio of reflected light to transmitted light in determining the quantity of gas. The gas detector can further include a light source having a bandwidth on the order of the absorption linewidth of the gas, such as in a range of between about 0.3 times the absorption linewidth of the gas and about seven times the absorption linewidth of the gas. The bandwidth of the light source can be in a range of between approximating the absorption linewidth the gas and about three times the absorption linewidth of the gas. The transmission bandwidth of the first etalon can be in a range of between approximating the absorption linewidth of the gas and about four times the absorption linewidth, such as in a range of between approximating the absorption linewidth the gas and about two times the absorption linewidth. The transmission bandwidth of the first etalon can be in a range of between about 10% and about 250% of the bandwidth of the light source, such as between about 25% and about 75% of the bandwidth of the light source.

The gas detector can further include a beam splitter that separates the light from the light source into a first beam directed to the first etalon, a second beam, and a second etalon configured to receive the second beam, the second etalon having a transmission bandwidth on the order of the absorption linewidth of the gas. The transmission bandwidth of the second etalon can be approximately equal and adjacent to the transmission bandwidth of the first etalon, with the transmission bandwidths of the first and second etalon each overlapping the absorption bandwidth of the gas and being substantially smaller than the bandwidth of the light source. The gas detector can further include a third detector for detecting light transmitted through the second etalon, and a fourth detector for detecting light reflected from the second etalon, with the processor determining the quantity of gas based on the transmitted and reflected light at the first and second etalon.

The processor can calculate the sum of ratios of reflected light and transmitted light at the first and second etalon in determining the quantity of gas. The transmission bandwidth of the second etalon can be in a range of between approximating the absorption linewidth of the gas and about four times the absorption linewidth, such as in a range of between approximating the absorption linewidth of the gas and about two times the absorption linewidth. The transmission bandwidth of the second etalon can be in a range of between about 25% and about 75% of the bandwidth of the light source.

Alternatively, the gas detector can further include a beam separator that separates the light from the light source into a first beam and a second beam, with a small deflection angle between the first beam and the second beam, thereby modifying the effective thickness of a single optical element for each beam and forming the first and second etalon in the optical element. The beam separator can include a beamsplitter, or, alternatively, a birefringent wedge. The deflection angle can be in a range of between about 0.25° and about 5°.

A method of detecting a gas can include receiving light from a light source through gas, the light source having a bandwidth on the order of an absorption linewidth of the gas, detecting a first portion of the light source bandwidth that coincides with at least a portion of the gas absorption linewidth, detecting a first remaining portion of the light source bandwidth, detecting an adjacent portion of the light source bandwidth that coincides with at least a portion of the gas absorption linewidth, detecting a second remaining portion of the light source bandwidth, and determining the quantity of gas based on the detected signals.

The method of detecting a gas can include directing the light from the light source to at least a first etalon having a transmission bandwidth on the order of the absorption linewidth of the gas, the transmission bandwidth of the first etalon being substantially smaller than the bandwidth of the light source. The method further includes detecting light transmitted through the first etalon, detecting light reflected from the first etalon, and determining the quantity of gas based on the detected signals. The method can further include separating the light from the light source into a first beam directed to the first etalon and a second beam, and receiving the second beam at a second etalon having a transmission bandwidth on the order of the absorption linewidth of the gas. The method further includes detecting light transmitted through the second etalon, and detecting light reflected from the second etalon, and determining the quantity of gas based on the detected signals. Alternatively, the method can include separating light from the light source into a first beam and a second beam, with a small deflection angle between the first beam and the second beam, detecting light from the second beam transmitted through the etalon, and detecting light from the second beam reflected from the etalon.

The gas detector has many advantages, including the potential for high sensitivity over long range for remote detection of gases.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The dual etalon receiver (DUET) described herein is a gas detector that relaxes some of the transmitter requirements by comprising a self-referencing receiver. The three major components of DIAL measurement noise that are considered for the purpose of the DUET receiver are: beam pointing overlap, source out-of-band light, and laser frequency stability in the presence of changing atmospheric absorption with wavelength ("atmospheric slope").

Beam-Pointing Overlap

Figure 1A:
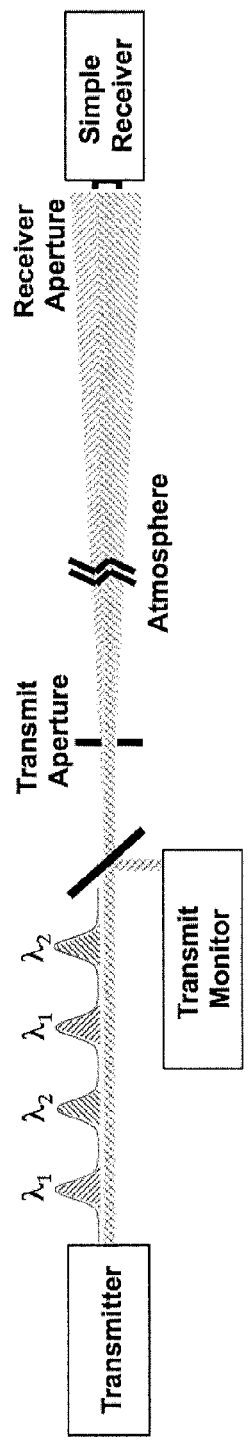
FIG. 1A is a schematic illustration of a prior art DIAL measurement.
Figure 1C:
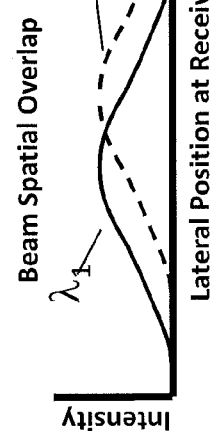
FIGS. 1B and 1C are graphs of intensity as a function of lateral position at the receiver in the DIAL measurement illustrated in FIG. 1A, showing examples of the effects of different beam propagation angles and modes. After propagation through the atmosphere, a receiver which subsamples the incident light can not make a meaningful measurement of the relative atmospheric transmission of the on- and off-absorption light without knowing the spatial profiles of the incident on- and off-absorption beams. One way to correct for this problem is to eliminate the need for all but one transmission wavelength.
Figure 1B:
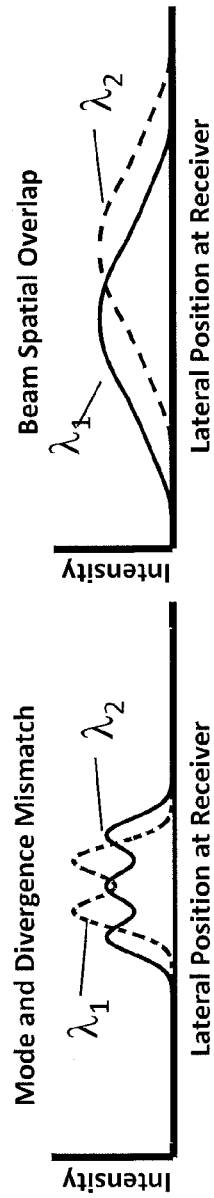

As shown in FIG. 1A, traditional DIAL requires that the transmitter alternate between two different frequencies, one on-resonance with a gas absorption, and the other off-resonance and therefore unaffected by the gas absorption. These frequencies typically are offset by 10-50 GHz, but they are still distinctly different outputs of the system. As the methods of generating coherent radiation are always frequency dependent, the system must change slightly to switch wavelengths. For example, a laser cavity can be lengthened, a different seed laser can be used, or even a non-linear amplification stage can be adjusted on a pulse-by-pulse basis. Unfortunately, in addition to adjusting the wavelength, any of these changes tend to modulate other properties of the source as well. Of primary concern is that different colors will tend to leave the source at slightly different angles, divergences, and spatial modes, as shown in FIGS. 1B and 1C. At short ranges, or with detectors that collect all of the transmitted light (a backscatter light detection and ranging (LIDAR) system with a large field of view), this is not an issue, but when a detector subsamples the beam, or after long propagation distances, it becomes problematic. This is the circumstance under consideration for the long-range bistatic sensing architecture described herein.

There are two ways to treat the source to eliminate this mode and pointing challenge. One way is to throw away all the light that doesn't have identical spatial characteristics by using aggressive spatial filtering, which comes with a large transmitted power cost. Alternatively, one can make the concentration estimate on a single-pulse basis. If this can be accomplished in a self-referencing manner, pointing and overlap issues are eliminated, and mode quality is unimportant as long as the same optical spectrum reaches all detectors.

Atmospheric Absorption

In the mid-wave infrared (MWIR), that is, at wavelengths in a range of between about 2 µm and about 5 µm, the atmosphere has several transmission windows of low absorption, but even within these bands, there is variation in atmospheric absorption on both the nanometer (nm) wavelength scale, and on the even finer GHz frequency scale. This fine atmospheric absorption structure causes two difficulties in performing a DIAL measurement. Firstly, broadband emission from parasitic processes in nonlinear laser gain stages typically have >10 nm of bandwidth (many hundreds of GHz). As shown in FIG. 2A, there can be many strong absorptions within a 10 nm band, even though there are regions within that band of very low absorption where one might operate. As a result, the total power measured before transmission through the atmosphere may be different from that which makes it through the atmospheric path to be measured and then to the receiver. This limits the possibility of using a reference detector at the transmitter to measure and remove pulse to pulse intensity fluctuations of the source.

Figure 2B:
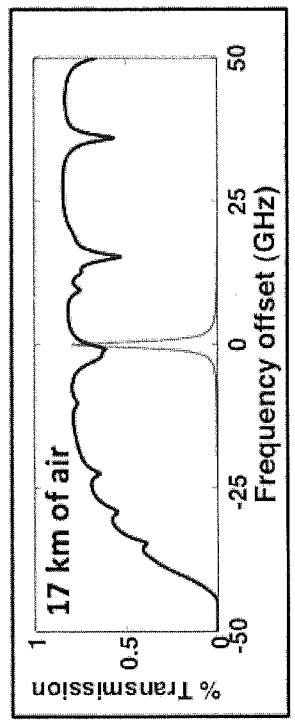
FIGS. 2A and 2B are graphs of % transmission as a function of wavelength spanning 100 nm (FIG. 2A) and frequency offset spanning 100 GHz (FIG. 2B) for atmospheric transmission around the CO overtone at 2.38 microns (μm). The shown transmission spectra are for 17 km of propagation through a middle latitude summer atmosphere, produced using the MODTRAN atmospheric simulation package (Spectral Sciences, Inc., Burlington, Mass.).
Figure 2A:
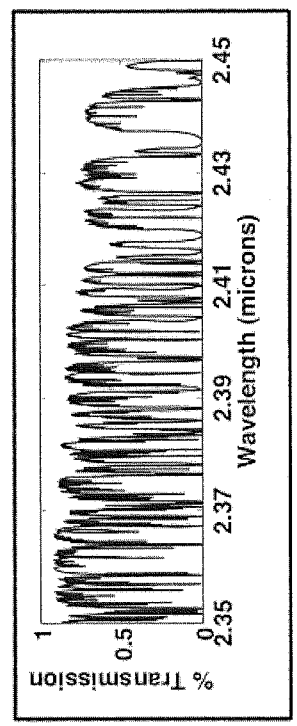

Secondly, on the GHz scale, the atmospheric absorption is not flat, as shown in the 2 nm (100 GHz) band illustrated in FIG. 2B. This slight atmospheric slope, of 5-10%/GHz means that if the laser frequency (shown as a sharp line at zero offset) drifts slightly, the static atmospheric absorption will also change. As laser frequency drifts are often slow, this error due to laser frequency drift is indistinguishable from a changing amount of trace target gas in the atmosphere.

The traditional way of dealing with both of these problems is to stabilize the source laser. Stabilizing pulse-to-pulse intensity fluctuations to better than 1% removes the need for a reference detector, thus obviating the difficulties caused by out-of-band light. Stabilizing the laser frequency eliminates clutter due to the atmospheric slope. Unfortunately, the required source frequency stabilization becomes more stringent at longer and longer ranges, as the atmospheric absorption profile necessarily becomes steeper with increasing range.

Another way of dealing with the frequency-induced noise sources would be to measure and remove their effect at the receiver by using a spectrally sensitive detector.

DUET Gas Detector and Method

To correct for the three clutter/noise terms that limit classical DIAL sensitivity at long range, a spectroscopically sensitive receiver is desirable. Instead of separating on- and off-absorption wavelengths in time by putting them in subsequent pulses, the light can be separated in the frequency domain by using a spectrometer as a receiver.

Any optical system, such as a grating or prism spectrometer, that can measure the optical spectrum in a single pulse would be capable of performing the measurement, given a laser pulse with a wider optical bandwidth than the absorption linewidth being measured. Collecting the spectrum, and taking the ratio of on-absorption to off-absorption power yields a measurement that is akin to that of canonical DIAL, except that it is performed on a single pulse basis instead of requiring two, temporally offset pulses.

Unfortunately, traditional spectrometers are not well suited for the active optical detection of gases composed of small molecules, such as $NH_3$, CO, HF, $H_2S$, $NH_3$, HCN, $C_2H_2$, $CH_4$, $C_6H_6$, $C_2H_6$, HCl, $CH_2O$, and HBr. The slits and gratings required in a grating spectrometer can be a source of loss, and require significant engineering effort to capture more than 10% of the incident light. Additionally, it is very challenging to achieve the dispersion equivalent to the 1-5 GHz-wide absorption linewidths (in MWIR) of the gases listed above, and hence sensitivity is sacrificed. What is needed is a simple spectroscopic element that uses as much of the received light as possible, and splits the light equally into two channels—'on-absorption' and 'off-absorption'.

Figure 3:
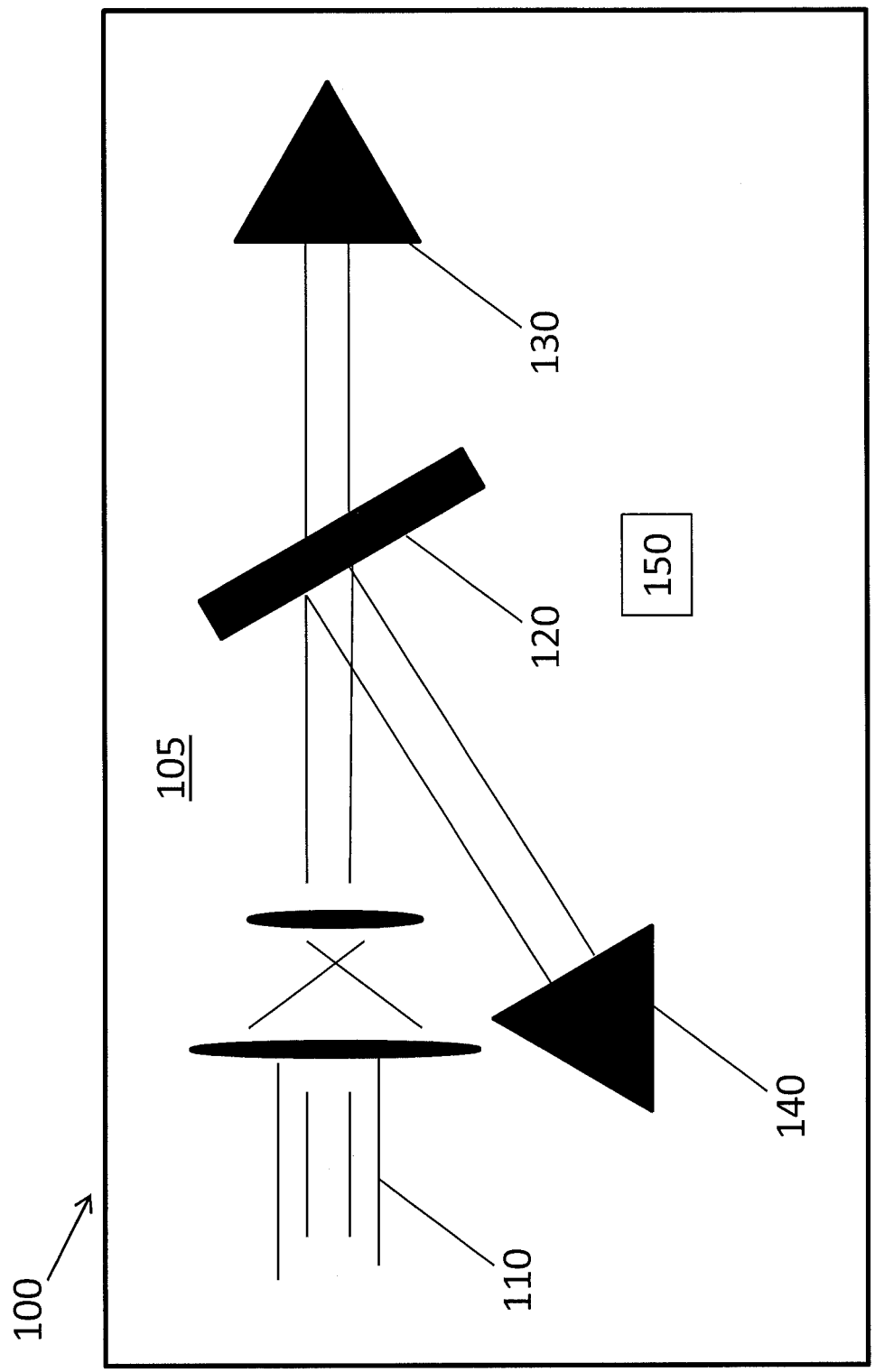
FIG. 3 is a schematic illustration of the optical setup for a single-etalon geometry for the gas detector.

As shown in FIG. 3, gas detector 100 includes receiver 105 configured to receive light 110 from a light source through gas, the light source having an optical bandwidth on the order of an absorption linewidth of the gas. Receiver 105 includes at least first etalon 120 having a transmission bandwidth on the order of the absorption linewidth of the gas, the transmission bandwidth of first etalon 120 being substantially smaller than the bandwidth of the light source. Gas detector 100 further includes first detector 130 for detecting light transmitted through first etalon 120, second detector 140 for detecting light reflected from first etalon 120, and processor 150 that determines the quantity of gas based on the detected transmitted and reflected light. Gas detector 100 can also include a light source (not shown) having a bandwidth on the order of the absorption linewidth of the gas, such as in a range of between about 0.3 times the absorption linewidth of the gas and about seven times the absorption linewidth of the gas. The bandwidth of the light source can be in a range of between approximating the absorption linewidth the gas and about three times the absorption linewidth of the gas. The transmission bandwidth of first etalon 120 can be in a range of between approximating the absorption linewidth of the gas and about four times the absorption linewidth, such as in a range of between approximating the absorption linewidth the gas and about two times the absorption linewidth. The transmission bandwidth of first etalon 120 can be in a range of between about 10% and about 250% of the bandwidth of the light source, such as between about 25% and about 75% of the bandwidth of the light source.

Figure 4:
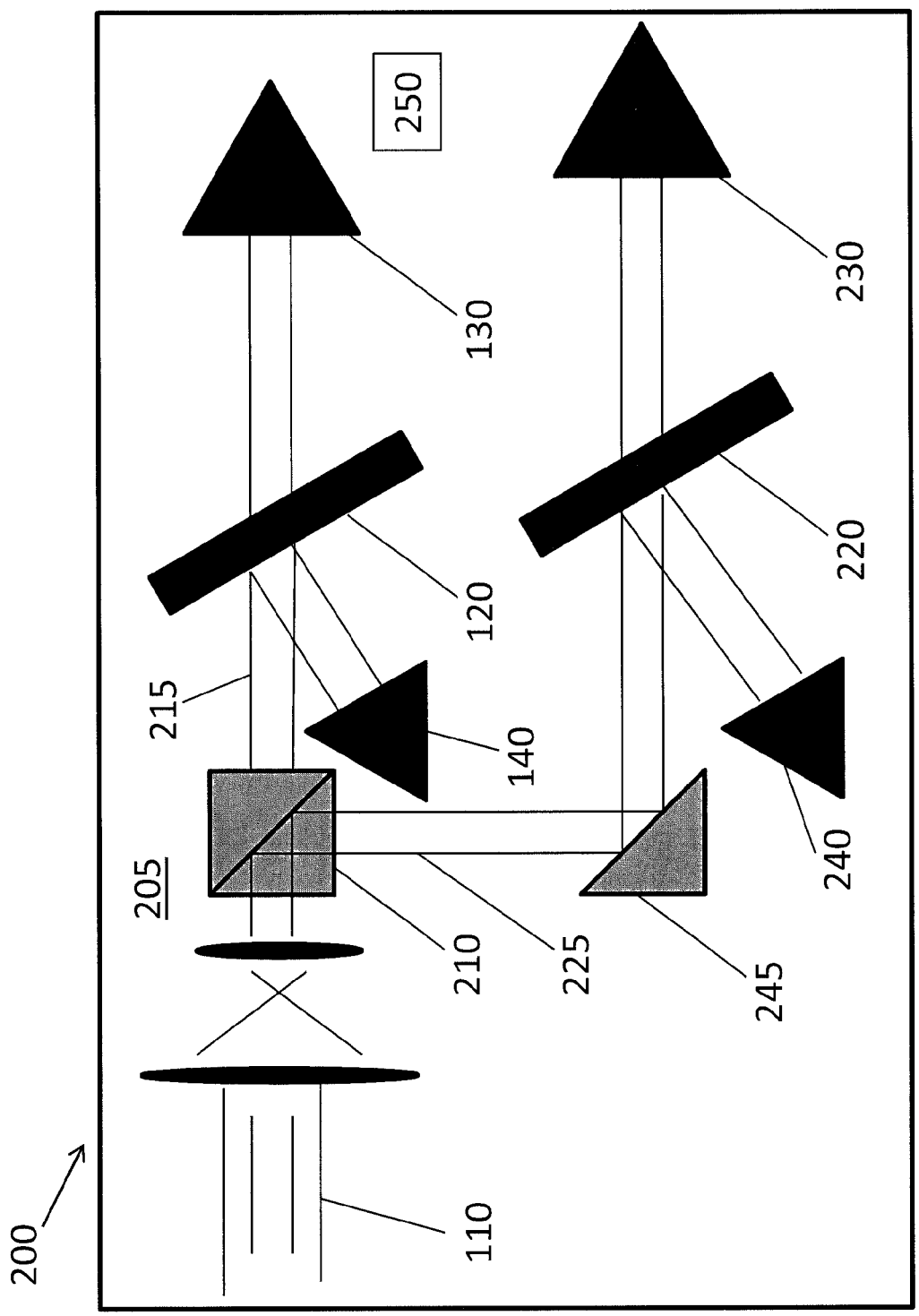
FIG. 4 is a schematic illustration of the optical setup for a dual-etalon geometry for the gas detector.

Alternatively, as shown in FIG. 4, gas detector 200 includes receiver 205 that includes the elements shown in FIG. 3, and further includes beam splitter 210 that separates light 110 from the light source into first beam 215 directed to first etalon 120, second beam 225, and second etalon 220 configured to receive second beam 225 from mirror 245, second etalon 220 having a transmission bandwidth on the order of the absorption linewidth of the gas. The transmission bandwidth of second etalon 220 can be approximately equal and adjacent to the transmission bandwidth of the first etalon, with the transmission bandwidths of first 120 and second etalon 220 each overlapping the absorption bandwidth of the gas and being substantially smaller than the bandwidth of the light source. Gas detector 200 further includes third detector 230 for detecting light transmitted through second etalon 220, and fourth detector 240 for detecting light reflected from second etalon 220, with processor 250 determining the quantity of gas based on the transmitted and reflected light at first etalon 120 and second etalon 220. The transmission bandwidth of second etalon 220 can be in a range of between approximating the absorption linewidth of the gas and about four times the absorption linewidth, such as in a range of between approximating the absorption linewidth of the gas and about two times the absorption linewidth. The transmission bandwidth of second etalon 220 can be less than or equal to about half the bandwidth of the light source.

Figure 5A:
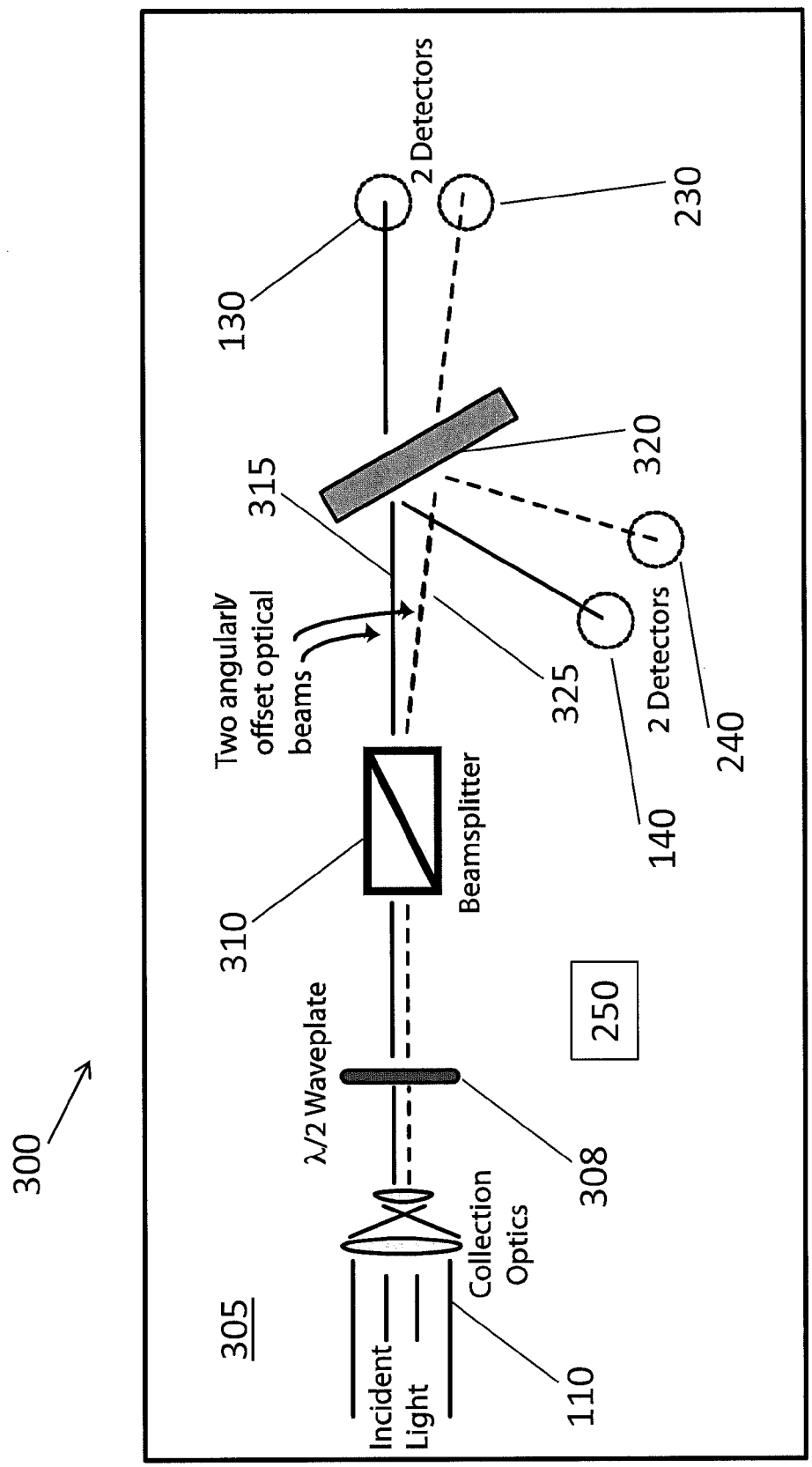
FIG. 5A is a schematic illustration of the optical setup for a dual-etalon geometry for the gas detector employing a single optical element in place of the first and second etalon, where two effective etalons are produced by utilizing the optical element at two different angles. The beamsplitter/waveplate combination separates incident light into two angularly offset beams, each of which interacts with the optical element to produce two effective etalons. The reflected and transmitted beams for each angle are measured using photo-detectors.

In yet another alternative, shown in FIG. 5A, gas detector 300 includes a receiver 305 that includes a single optical element 320 that takes the place of first etalon 120 and second etalon 220 of FIG. 4, by separating light 110 from the light source into two angularly offset optical beams, 315 and 325, using a beam separator comprising a combination of half-waveplate (i.e., $\lambda/2$) 308 and beamsplitter 310 that introduces a small deflection angle between first beam 315 and second beam 325. The small deflection angle modifies the effective thickness of optical element 320 for each beam, and thus produces two effective etalons with two transmission bandwidths similar to those shown in FIG. 11A, while employing optical element 320. The deflection angle can be in a range of between about 0.25° and about 5°.

Figure 5B:
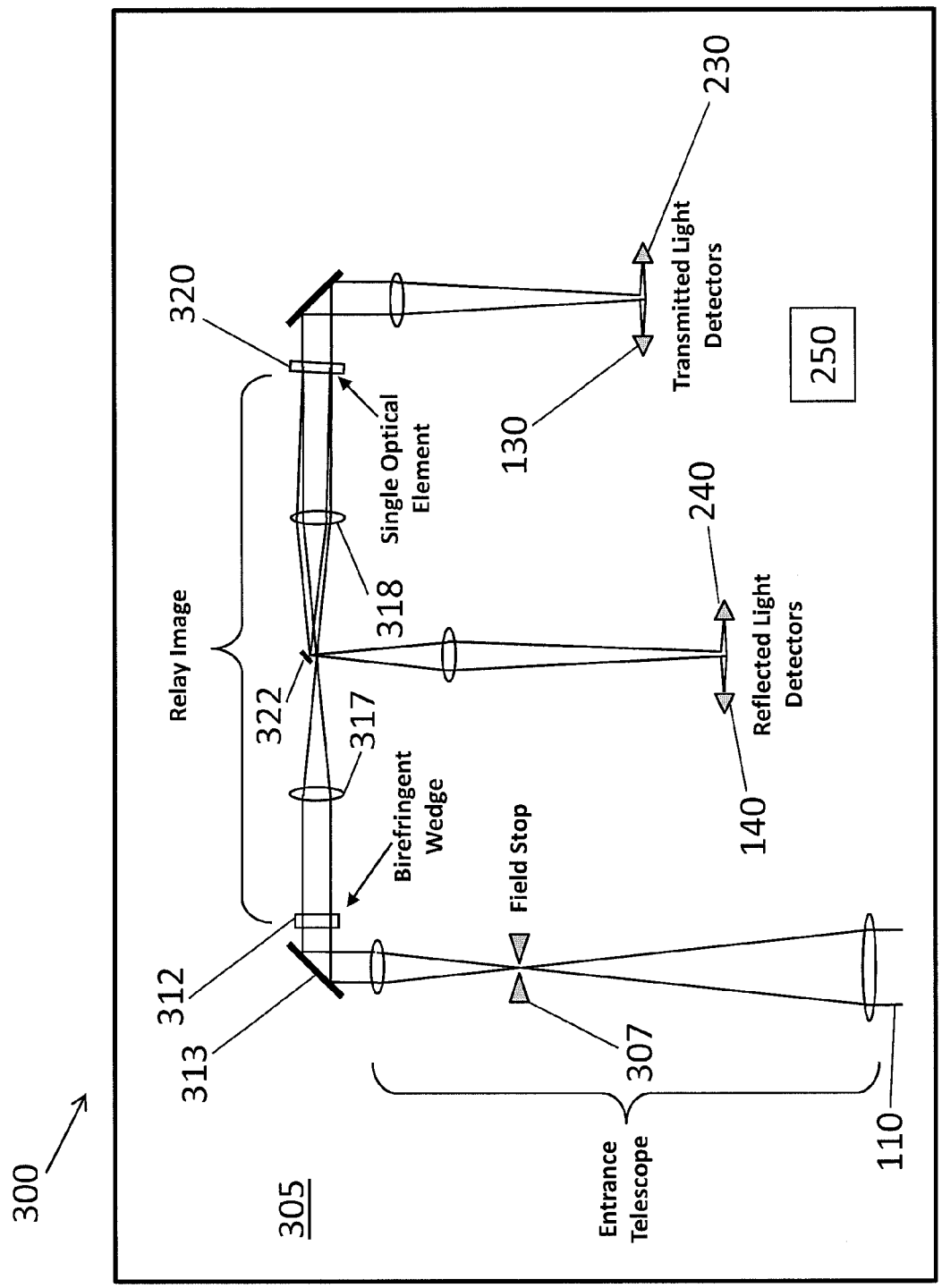
FIG. 5B is an illustration of an optical design according to this invention that takes advantage of a relay-image design to minimize walk-off between the two incident beams, and to enable the beams reflected from the etalon to be separated from the incident beams at an intermediate focus, while maintaining near-normal incidence on the etalon.

In still another alternative, shown in FIG. 5B, gas detector 300 includes a receiver 305, wherein the front of the optical system is a 0.4× afocal telescope to increase the light gathering power of the system. Receiver 305 also includes a field stop 307 at the internal focus of the telescope. This field stop 307 limits the field of view of the optical system and thereby prevents the angle of the light rays incident on the etalon from exceeding the angles over which the system retains its performance. As the etalon transmission maxima shift with incident angle, this field of view must be constrained to within about 500 microradians before the transmission maxima move too far off the target gas absorption linewidth. After exiting the telescope, a steering mirror 313 then sends the collimated light into a beam separator comprising a birefringent wedge 312, which serves to separate the incident light 110 into two polarizations and introduces a small deflection angle between them. The deflection angle can be in a range of between about 0.25° and about 5°. Having the beams hit the optical element 320 at two different angles effectively creates two etalons with their transmission maxima offset, as required for the two-etalon design. Rotation of the birefringent wedge 312 produces a small change of direction of the transmitted beams, but, more importantly, slightly changes the angle between the two beams. This rotation enables the frequency separation or offset between the two effective etalons to be optimized. The exit face of the wedge 312 is then relay-imaged onto the optical element 320 by two matched lenses 317 and 318 separated by twice their focal lengths. This design choice maintains the spatial overlap of the two polarizations at the surface of optical element 320 (and preserves the angular difference which creates the two effective etalons). Without the relay image, the two polarizations begin to walk off of each other as they propagate toward the etalon, limiting the size of the optical beam or requiring larger optics. This optical design additionally enables the beams reflected from the optical element 320 to be separated from the incident beams while still maintaining near-normal incidence by introducing a small mirror 322 at the intermediate focus created between the wedge 312 and optical element 320. In this design, the two polarizations are separated in angle vertically, which puts their foci above each other at the intermediate focus. The optical element 320 is tilted slightly off-normal in the horizontal plane, separating the foci of the two reflected polarizations horizontally from the foci of the incident beams. A small mirror 322 can then be inserted at the focus to just "pick off" the reflected beams and send them at 90 degrees toward their detectors 140 and 240. Both reflected and transmitted beams are focused with additional optics and the polarizations, which are separated vertically, are intercepted before their focus and sent to four separate detectors (140, 240, 130, 230).

This optical arrangement exhibits higher optical efficiency than the design shown in FIG. 5A, in part by removing the 50-50 power splitting beamsplitter 310, and minimizes optical aberration by keeping the beams close to centered on all powered optical elements. Additionally, each sub-element can be separately aligned (telescope, 1:1 relay imaging system, detector focusing optics) before being installed in final form.

Fabry-Perot Etalons

Figure 6:
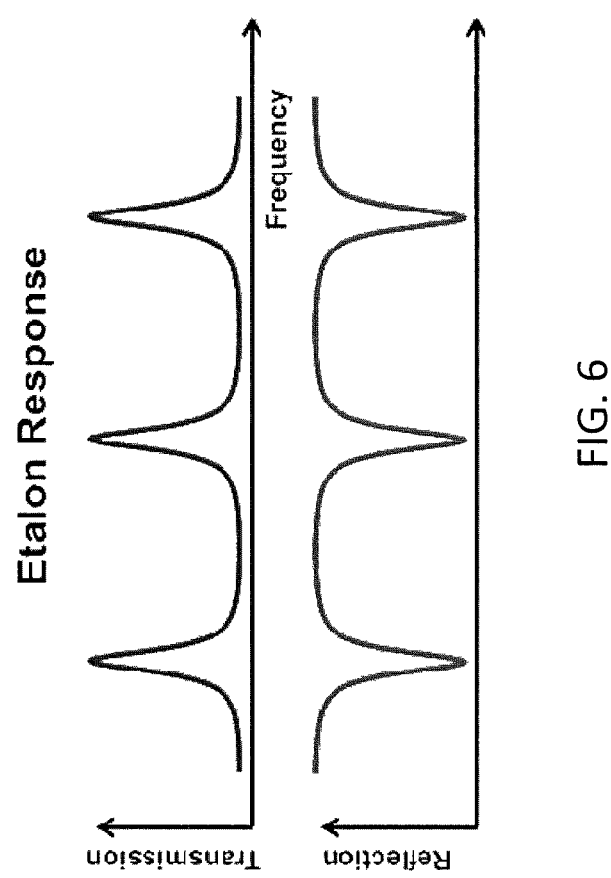
FIG. 6 is a graph of Fabry-Perot etalon response in transmission and reflection as a function of frequency. The transmission spectrum of an etalon is periodic, with maxima in transmission corresponding to constructive interference of the partially transmitted beams off the two reflective surfaces.

The core element of a wavemeter, a resonant cavity in the form of a Fabry-Perot etalon, can fulfill the requirement of splitting incident light equally into two channels—"on-absorption" and "off-absorption." An etalon has two parallel partially reflective surfaces, separated by a macroscopic (typically a few mm) distance. Light transmitted through the structure partially reflects off the two surfaces. Partial reflections that constructively interfere are primarily reflected, while destructive interference results in transmission, as shown in FIG. 6.

As dielectric mirrors have minimal absorption losses, all of the incident light is either reflected or transmitted by the mirrors. The spacing between the maxima of transmission is the free spectral range (FSR) of the etalon, and scales with the mirror separation: FSR=c/(2·n·d), where c is the speed of light, n is the index of refraction of the medium between the reflective surfaces, and d their separation. The transmission bandwidth (full width at half maximum (FWHM)) of the etalon is a function of the ratio of FSR to the finesse of the etalon (a function of the mirror reflectivity). With R denoting the reflectivity of one of the partially reflecting surfaces, k the one-way loss due to absorption in the etalon, and $\delta = 2\pi V/FSR$, the functional form of etalon response is $$et_{trans} = \frac{k^2(1-R)^2}{R^2k^4 - 2Rk^2\cos(\delta) + 1} \quad (1)$$

$$et_{refl} = \frac{R(k^4 - 2k^2\cos(\delta) + 1)}{R^2k^4 - 2Rk^2\cos(\delta) + 1}$$

Taking the ratio of reflected/transmitted leaves, $$\frac{et_{refl}}{et_{trans}} = \frac{R(k^4 - 2k^2\cos(\delta) + 1)}{k^2(1-R)^2} \approx \frac{2R(1-\cos(\delta))}{(1-R)^2} \quad (2)$$

For a Gaussian laser pulse with a full width at half maximum (FWHM) of $\Delta v$, centered on one of the etalon maxima, the total transmission is $$\int I_0 et_{refl} e^{-4ln2(\frac{v-v_0}{\Delta v})^2} \quad (3)$$

Taking the ratio with the reflected response yields $$S_{et} = \frac{\int et_{refl} e^{-4ln2(\frac{v-v_0}{\Delta v})^2} dv}{\int et_{trans} e^{-4ln2(\frac{v-v_0}{\Delta v})^2} dv} \quad (4)$$

the most important part of Eq. 4 being that the $I_0$ terms cancel, yielding a response which is independent of total received power, and only a function of etalon response, pulse bandwidth and frequency, and possible absorption. This integrated response is defined as the etalon signal ($S_{et}$).

Single-Etalon Measurements of Absorbance

Figure 7:
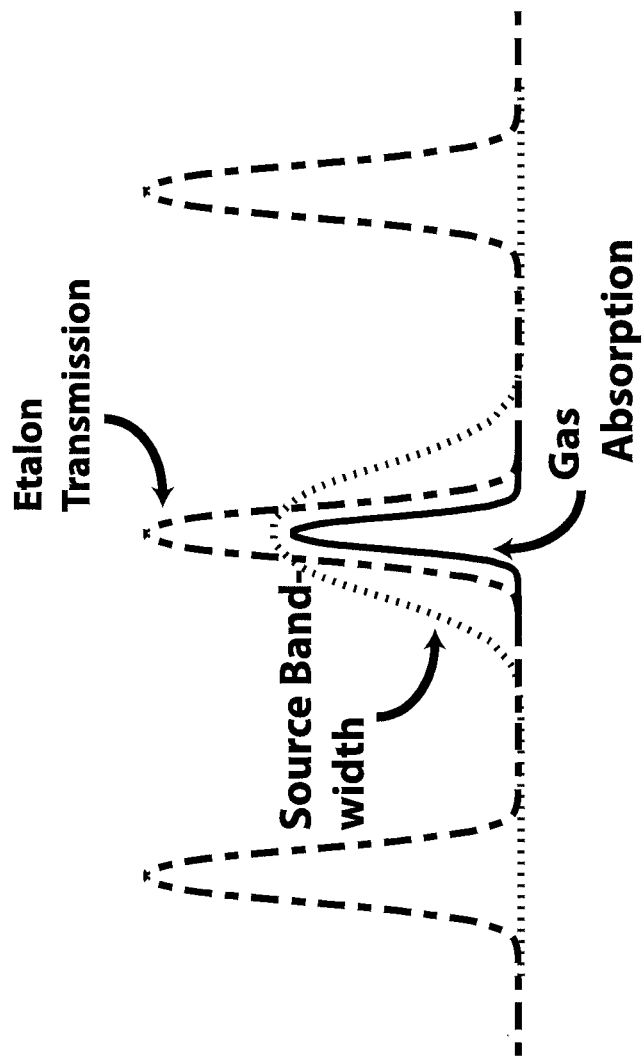
FIG. 7 is an illustration of relative frequency alignment of the single etalon geometry. For the single etalon configuration, both the transmission spectrum of a single etalon (dashed line), and the center frequency of the transmitted source (dotted line) are centered on the frequency of the absorption line of the gas to be measured.
Figure 8:
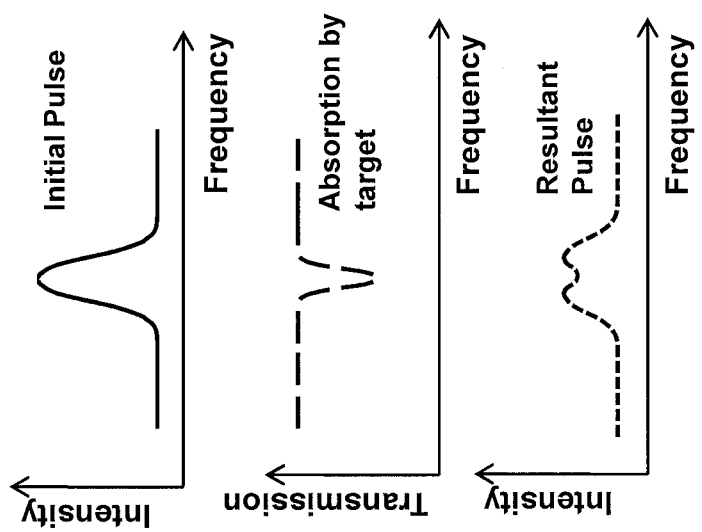
FIG. 8 is an illustration of molecular absorption effects on a broadband source, shown lined up with a single etalon transmission maximum.

Consider a single etalon transmission band to be an extremely narrow-band interference filter, centered on, and similar in frequency width to (i.e., on the order of) a molecular absorption linewidth. With a sufficiently large etalon FSR (typically >10-20 GHz), other etalon transmission maxima are outside of any reasonable source optical bandwidth, and can be neglected. The simplified scheme shown in FIG. 3 tunes one etalon transmission band to the absorption line of a molecule of interest. As shown in FIGS. 7 and 8, this scheme uses the etalon as a reflective filter that preferentially transmits light that corresponds to the molecular absorption feature, and reflects the light that does not. The resultant signal is shown in FIG. 8. The intensity of the light received through the gas is inversely proportional to concentration of the molecule of interest, and, because the etalon is narrowly tuned to the absorption line, as shown in FIG. 7, the received light intensity is not affected by other gases. Furthermore, as only the term in the denominator of $S_{et}$ is significantly changed by absorption, $S_{et}$ is inversely proportional to transmission through the probed absorption feature, and thus directly proportional to concentration, while maintaining its insensitivity to overall pulse intensity.

Figure 9A:
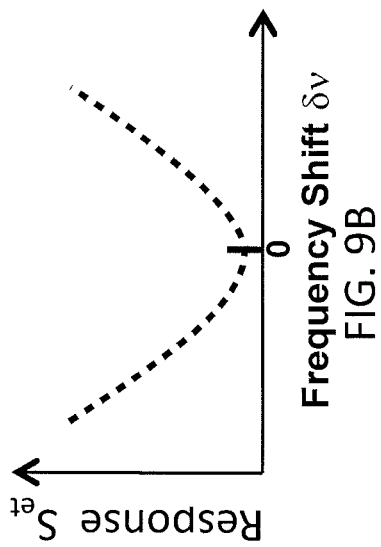
FIGS. 9A and 9B are illustrations of etalon response ($S_{et}$, the ratio of reflected to transmitted light, defined as a function of the relative frequency shift $\delta v$ between laser center frequency and etalon frequency. When centered (aligned) to each other, a frequency shift in either direction is indistinguishable, due to symmetry.
Figure 10A:
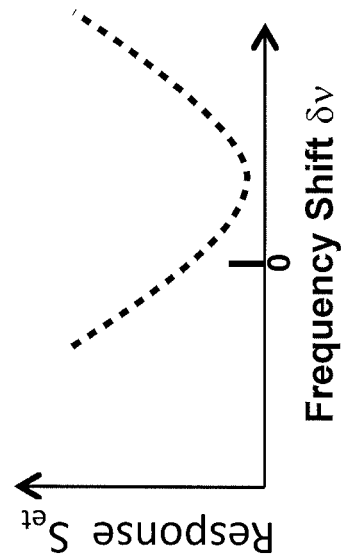
FIGS. 10A and 10B are illustrations of inducing a small static frequency shift in the etalon response shown in FIGS. 9A and 9B, whereby the symmetry shown in FIGS. 9A and 913 is broken, enabling an estimate of small frequency movement of the optical source or etalon transmission bandwidth to be made.
Figure 9B:
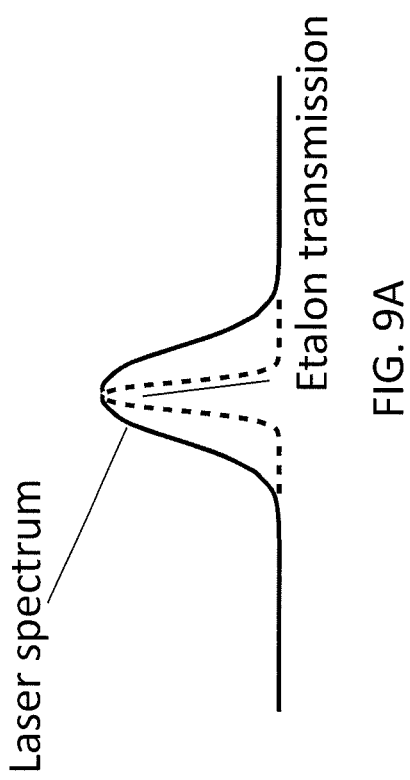
Figure 10B:
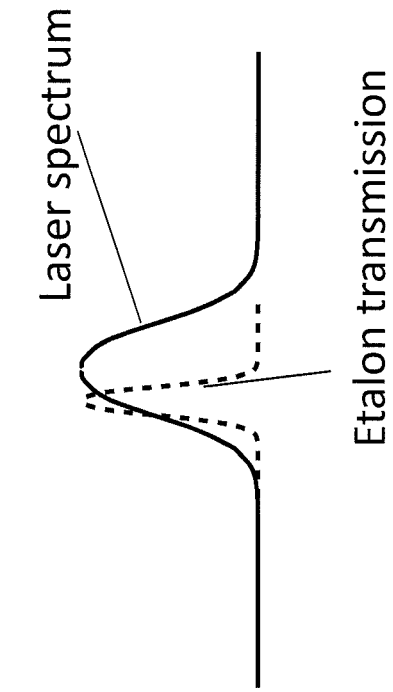

A disadvantage of this scheme is that $S_{et}$ is effectively a two channel spectrometer, and thus requires that the light source bandwidth, absorption line frequency, and spectrometer frequency be perfectly aligned, as shown in FIGS. 7, 9A and 9B. To the extent that the optical source spectrum and etalon transmission bandwidth can jitter or slowly drift in frequency, as shown in FIGS. 10A and 10B, such changes in frequency relative to the absorption line center are indistinguishable from changes in absorption by the gas of interest. In a traditional spectrometer, both spectrometer and source frequencies would be locked to the absorption line of interest, but the strenuous levels of frequency stability required for a high-sensitivity, long range DIAL measurement make this technically challenging. As an alternative, the receiver can be designed to be self-calibrating by adding a second, offset etalon filter.

Dual-Etalon Measurements of Absorbance

The problem with the single etalon design is that drift in the relative frequency of laser and etalon transmission frequency tends to lower the relative amount of light transmitted by the filter, and conversely increase the amount of light reflected. Even worse, as shown in FIG. 9A, since both the laser bandwidth and etalon transmission are symmetrically shaped in frequency (Gaussian and Lorentzian, respectively), and nominally centered on each other, relative drifts in either direction are indistinguishable, that is, the response increases for a positive or negative $\delta v$, as shown in FIG. 9B.

Figure 11A:
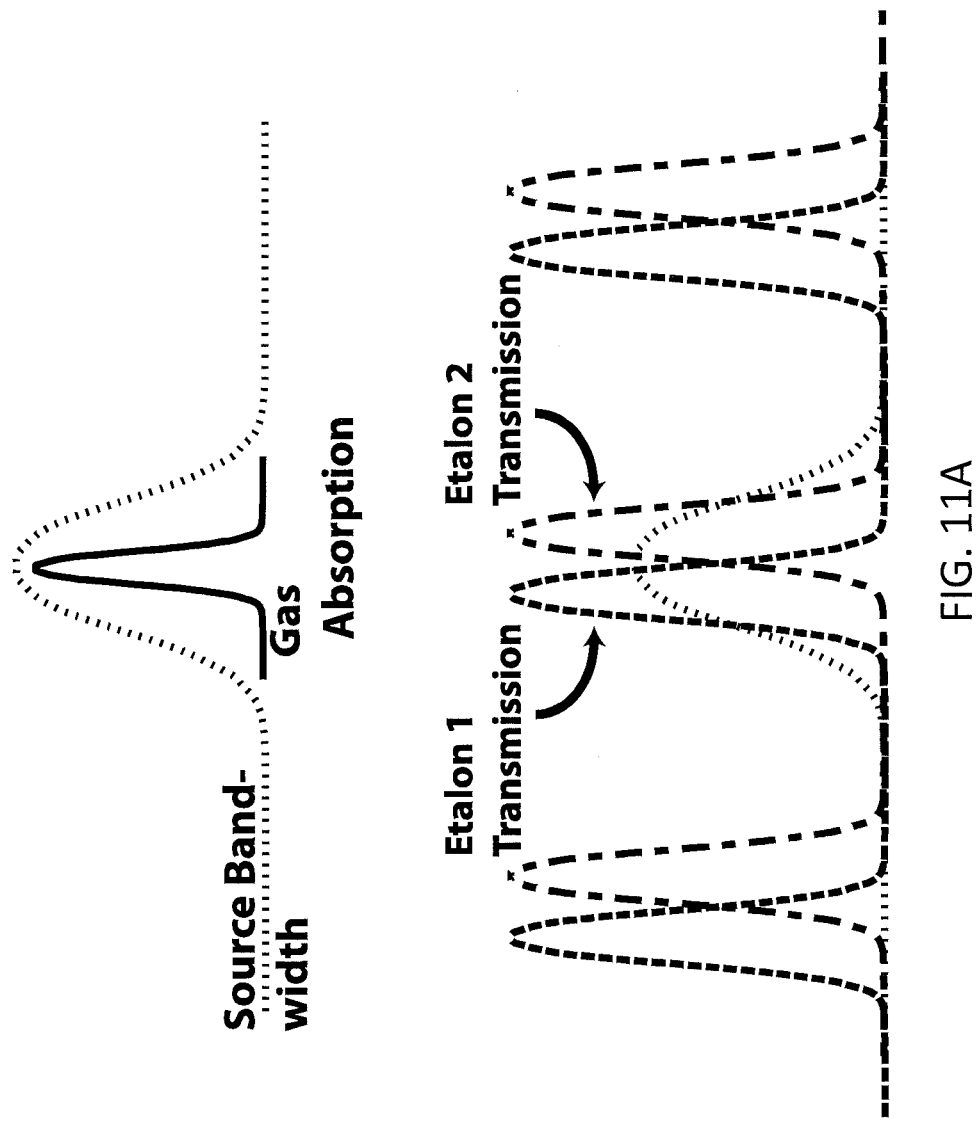
FIG. 11A is an illustration of relative frequency alignment of the dual etalon geometry. For the dual etalon configuration, the center frequency of the optical source (dotted line) is nominally centered on the center frequency of an absorption line of the gas to be measured. The two etalon transmission maxima are offset to either side of the gas absorption.
Figure 11B:
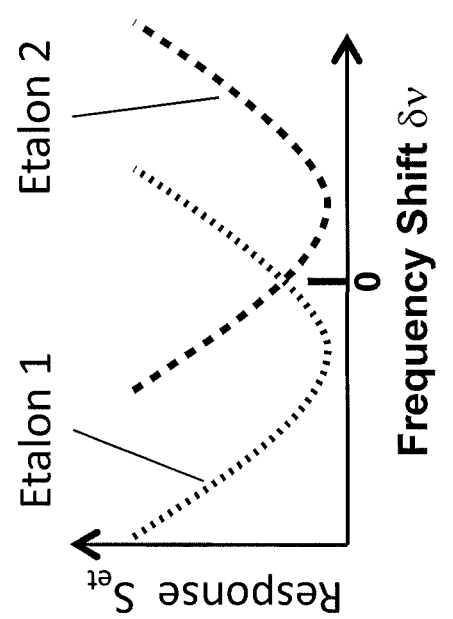
FIG. 11B is an illustration of two etalons with equal and opposite frequency offsets relative to the gas absorption line center, showing their relative responses due to frequency shift of the laser source. This is only true as long as the two etalons remain locked to one another.

The dual etalon approaches of FIGS. 4 and 5 overcome the above problem. First, consider a single etalon with its transmission bandwidth shifted off the source optical spectrum maximum (and hence also shifted off the maximum of the molecular absorption). As shown in FIGS. 10A and 10B, this frequency offset resolves the positive/negative ambiguity, and enables the measurement of relative frequency drift, much like an edge filter does in Doppler wind speed measurements. As shown in FIG. 11A, as long as the shift is relatively small (about 1 GHz, determined by the exact etalon geometry), the structure retains almost all of its sensitivity to molecular absorption, because the transmission band of each etalon still overlaps with a substantial portion of the gas absorption linewidth.

Shifting the etalon to the opposite sign in frequency shift (a mirror image of FIG. 10B) reverses the sense of the asymmetrical frequency-shift response: if before an increase in laser frequency induced an increase in the etalon response ($S_{et}$), switching the offset direction now reduces the etalon response with increase in laser frequency.

This suggests an architecture in which incident light is split into two paths, where each path is incident on etalons which are identical except for the position of their frequency maxima—one on one side of the absorption line, the other equally spaced on the other side, as shown in FIG. 11A. For small values of frequency shift ($\delta v$), merely summing the responses of these two etalons will, to first order, cancel out the effects of frequency shift, but maintain the sensitivity to molecular absorption. We define two new parameters ($S_+$ and $S_-$) in terms of the $S_{et}$ of the two different offset etalons.

$$S_+ = \frac{S_{et_1} + S_{et_2}}{2} \quad (5)$$

$$S_- = \frac{S_{et_1} - S_{et_2}}{2}$$

Here, $S_+$ is equivalent to the single etalon response previously discussed, and exhibits the same sensitivity to concentration, but with some added robustness to small shifts in relative frequency. $S_-$ is independent of any change in concentration, since it only retains antisymmetric changes in response; that is, it is a good metric of the magnitude of frequency shift, and can be used as a proxy for $\delta v$ allowing the removal of effects of relatively large frequency shifts. We define a corrected signal $S_{corr}$ (Eq. 6) that is related only to measured absorption, and independent of frequency shift, where $k_i$ are empirical constants that can be numerically calculated from the overlap integrals in equations 3 and 4. For modest shifts of less than a quarter of the etalon FSR in either direction, only the first 4 to 6 terms of the sum (i.e., $n \le 6$ in Eq. 6 below) are typically required to remove nearly all of the frequency shift effects. $k_0$ is defined such that when the absorption by the molecular species is zero, $S_{corr}$ is also 0.

$$S_{corr} = S_+ + \sum_{i=0}^{n} k_i S_-^i \qquad (6)$$

Figure 12:
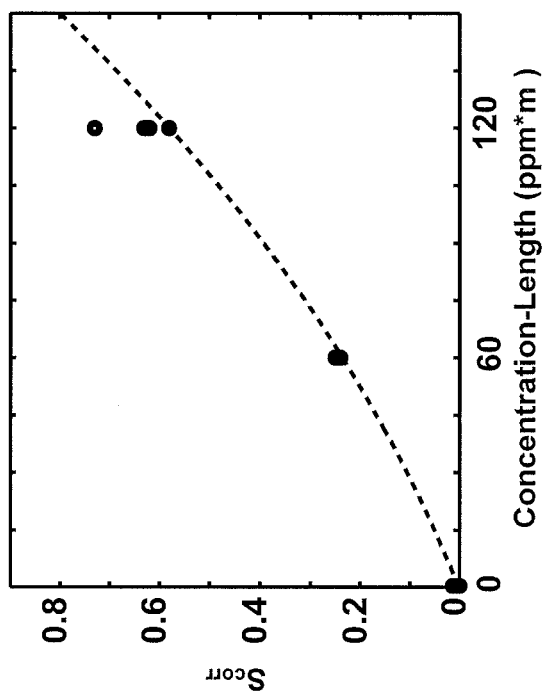
FIG. 12 is a graph of $S_{corr}$ as a function of molecular species concentration-length product (C-L), with several experimentally measured points indicated. In the low concentration limit, the C-L is directly proportional to $S_{corr}$, with a proportionality factor, as in traditional DIAL, of some fraction of $\pi \cdot \Gamma/(S \cdot n_{air})$, where $\Gamma$ is the air-broadened half-linewidth (half width at half maximum (HWHM)), S is the absorption line strength, and $n_{air}$ is the molecular density of air.

This produces a single metric for concentration length, shown in FIG. 12. The signal $S_{corr}$ is directly proportional to concentration-length (i.e., linear) at low concentrations, with a scale factor related to the molecular species absorption strength and linewidth, and the etalon FSR, finesse, and offset. There is a slight superlinear (i.e., nonlinear) response at very high concentrations, as the absorption of the target begins to affect the reflected channel more at higher concentrations.

A method of detecting a gas using a gas detector can include receiving light from a light source through gas, the light source having a bandwidth on the order of an absorption linewidth of the gas. The method includes detecting a first portion of the light source bandwidth that coincides with at least a portion of the gas absorption linewidth, and detecting a first remaining portion of the light source bandwidth. The method can further include detecting an adjacent portion of the light source bandwidth that coincides with at least a portion of the gas absorption linewidth, detecting a second remaining portion of the light source bandwidth, and determining the quantity of gas based on the detected signals.

The method of detecting a gas using gas detector 100, shown in FIG. 3, can include directing the light 110 from the light source to at least first etalon 120 having a transmission bandwidth on the order of the absorption linewidth of the gas, the transmission bandwidth of first etalon 120 being substantially smaller than the bandwidth of the light source. The method further includes detecting light transmitted through first etalon 120, detecting light reflected from first etalon 120, and determining the quantity of gas based on the detected signals. The method can further include using a gas detector 200, as shown in FIG. 4, for separating light 110 from the light source into first beam 215 directed to first etalon 120 and second beam 225, and receiving second beam 225 at second etalon 220 having a transmission bandwidth on the order of the absorption linewidth of the gas. The method further includes detecting light transmitted through second etalon 220, and detecting light reflected from the second etalon 220, and determining the quantity of gas based on the detected signals. Determining the quantity of gas can include calculating the sum of ratios of reflected light to transmitted light at the first and second etalon. Alternatively, the method can include using a gas detector 300, shown in FIGS. 5A and 5B, for separating light 110 from the light source into first beam 315 and second beam 325, with a small deflection angle between first beam 315 and second beam 325, detecting light from second beam 325 transmitted through etalon 320, and detecting light from second beam 325 reflected from etalon 320. The deflection angle can be in a range of between about 0.25 degrees and about five degrees.

Source Bandwidth Requirements

Assuming an optimally designed etalon for a given absorption linewidth and source bandwidth, the ultimate sensitivity of the receiver is a function of the ratio of source bandwidth to absorption linewidth. The method requires that a single pulse of light contain enough on-absorption and off-absorption light to enable a good comparison—ideally, as much on-resonance light would be used as off-resonance light to maximize sensitivity at the furthest operating range, but the continuous, gradual nature of the etalon filter provides that the ratio between on-resonance and off-resonance light does not have to be exactly half.

Figure 13:
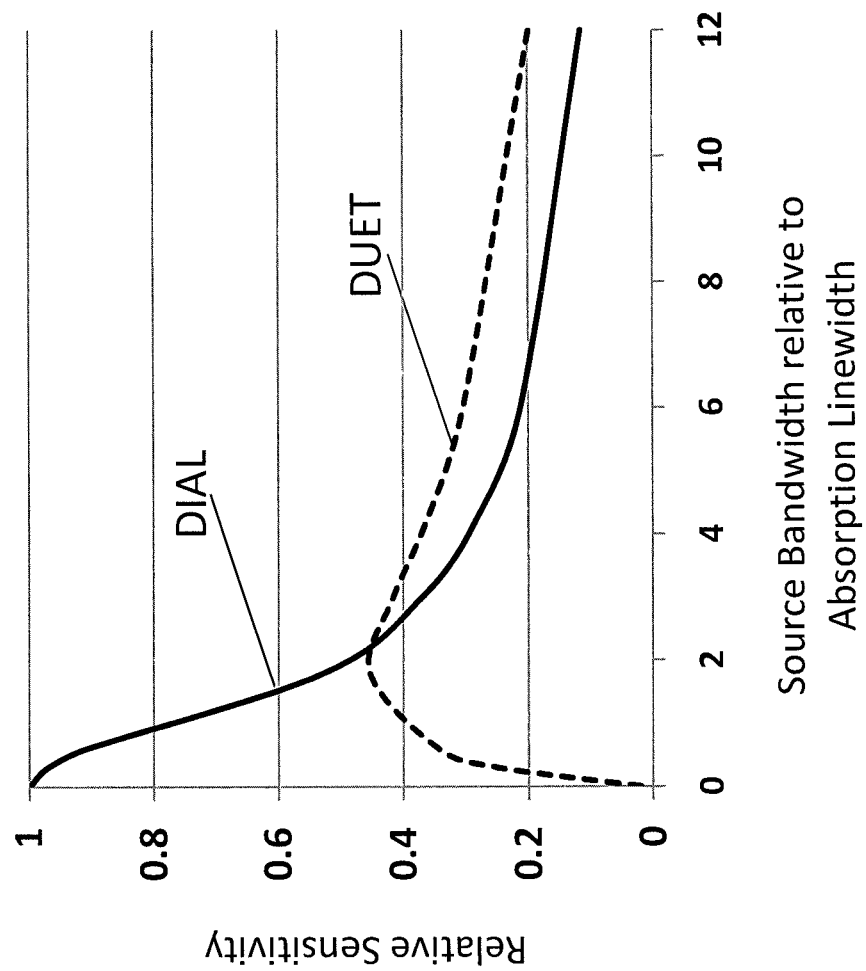
FIG. 13 is a graph of relative sensitivity as a function of the ratio of source bandwidth to absorption linewidth.

FIG. 13 is produced by numerically calculating the integrals in Eq. 4, and comparing the sensitivity of the DUET gas detector to that of 2-color DIAL for an extremely narrow-band (delta-function-like) source. This result considers only the relationship between fully processed (unitless) signal and measured concentration, and ignores the effect of relative signal-to-noise (SNR) or the number of signal averages possible in a given time.

Etalon Design

For a given source optical bandwidth and absorption linewidth the ideal etalon maximizes sensitivity while placing, at zero CL, equal amounts of light on all four detectors. To perform this optimization, a figure of merit (FOM) is defined as, $$FOM = \log \frac{\partial S_{et}}{\partial CL}\bigg|_{CL=0} - \mathrm{abs}(\log(S_{et}|_{CL=0})) \qquad (7)$$

with optimal sensitivity occurring with maximal values of FOM. Here, the first term, $$\log \frac{\partial S_{et}}{\partial CL}\bigg|_{CL=0} \qquad (8)$$

corresponds to the sensitivity at 0 concentration, with the second term, $$-\mathrm{abs}(\log(S_{et}|_{CL=0})) \qquad (9)$$

being the penalty due to unbalanced power distribution between the reflected and transmitted light detectors.

Numerically calculating this figure of merit for varying values of etalon FSR, finesse, and etalon-offset produces a 3-D surface (not shown).

Etalon Considerations

The ideal version of a dual etalon gas detector would work with consistent sensitivity over a large frequency bandwidth, and with an arbitrary input aperture. Additionally, each etalon would precisely separate light into 'in-band' and 'out-ofband' channels (light that was of the right frequency to see molecular absorption, and light out of that frequency band). As all of these demands place conflicting requirements on the system design, it is necessary to do a parametric search to find an optimized design.

The variables that can be adjusted, and their principal effects are summarized in Table 1.

TABLE 1

Dual Etalon Design Parameters

| Design Parameter | Principal effect | Range | Optimal | Limitations |
|---|---|---|---|---|
| $\frac{\text{Etalon FSR}}{\text{EtalonFinesse}}$ | Sets etalon transmission bandwidth | 1-4 times the target gas absorption linewidth | ~1.2 times the target gas absorption linewidth | High finesses require difficult optical coatings, Small FSR |
| $\frac{\text{Etalon FSR}}{\text{EtalonFinesse}}$ | Sets etalon transmission bandwidth | 10% to 250% of source bandwidth | 50% of source bandwidth | requires precise optical cavities |
| Etalon Frequency Offset | Sets the limits of frequency jitter correction (S__) | 10% to 100% of etalon transmission bandwidth | 50% of etalon transmission bandwidth, depending on level of frequency noise rejection required | Offset comes at the cost of absolute sensitivity. Highest system sensitivity is obtained with no offset. |
| Source bandwidth | Source of on-resonance and off-resonance light for the differential absorption measurement | 0.3-7 times the absorption linewidth | 2.2-2.8 times the absorption linewidth | Too much bandwidth or too little bandwidth reduces sensitivity |
| Etalon average reflection over source bandwidth | Sets the average power seen by all four photodetectors | 25% to 75% | 50% | Determined by choices in above parameters, not independent. |

Optimization entails getting the highest sensitivity practical for a given source bandwidth to absorption linewidth ratio. This large solution space can be studied in simulation, numerically solving for the reflected and transmitted signal due to offset etalon transmissions with increasing concentration of absorbing species. With the large parameter space to be studied, some optimizations to reduce the number of studied variables are helpful.

Figure 14A:
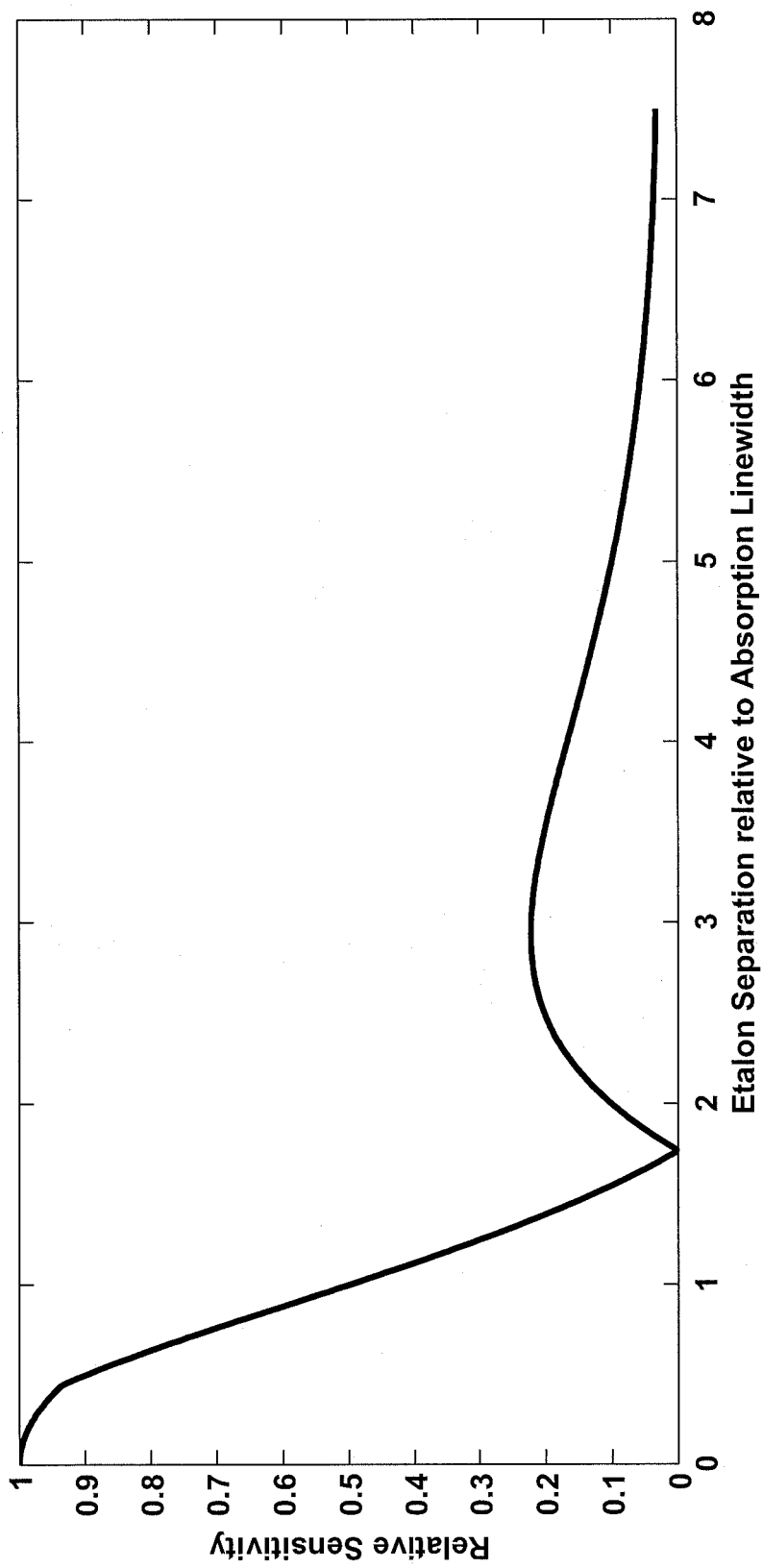
FIG. 14A is a graph of relative sensitivity as a function of etalon separation relative to absorption linewidth, showing the effect of varying etalon separations on system sensitivity to gas. Shown is the relative sensitivity of the dual-etalon geometry, when varying the frequency separation between the two etalon maxima. The graph is for the optimal source bandwidth equal to about 2.5 times the absorption linewidth.

First, consider the optimal source bandwidth case obtained from FIG. 13, with the laser source having 2.5 times the bandwidth of the molecular absorption. Secondly, the etalon FSR is fixed at a relatively large 20 GHz; which is easily fabricated, and doesn't require difficult etalon finesses at the optimal sensitivities. Lastly, Eq. 7 is solved for the FOM while varying etalon finesse and offset to produce FIGS. 14A and 14B.

Figure 14B:
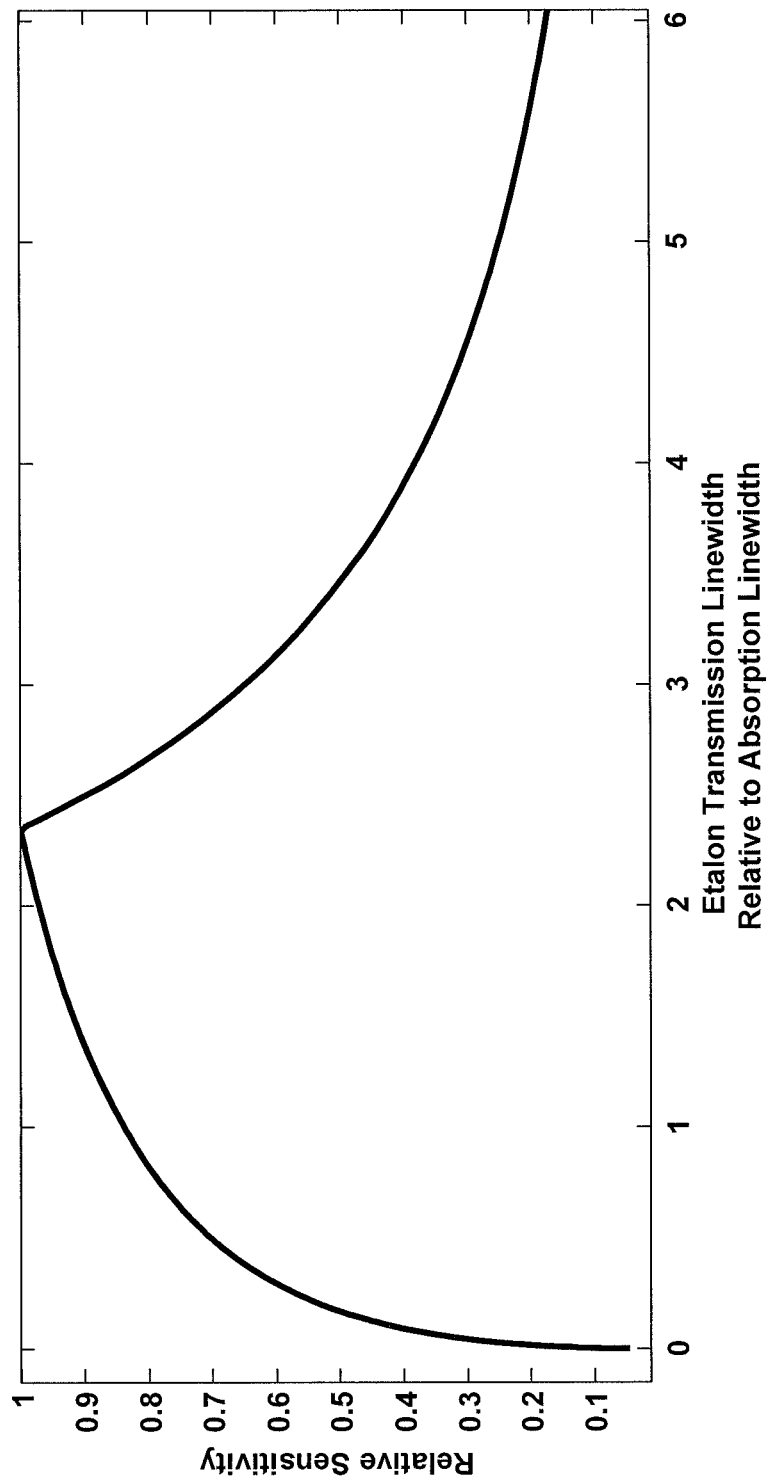
FIG. 14B is a graph of relative sensitivity as a function of etalon transmission bandwidth relative to absorption linewidth, showing the effect etalon transmission bandwidth on system sensitivity to gas. Shown is the relative sensitivity of the dual-etalon geometry, when varying the bandwidth of the etalon transmission maxima. The graph is for the optimal source bandwidth equal to about 2.5 times the absorption linewidth.

Based on this example analysis, and assuming a representative 2 GHz molecular absorption linewidth (FWHM), the optimal etalon transmission bandwidth to absorption linewidth ratio is about 2.3 (as shown in FIG. 14B), indicating a finesse of about 4.3 for a 20 GHz FSR etalon. This corresponds to an etalon reflectivity of about 50%. A reflectivity of this order is easily achieved with dielectric coatings, and is close to the native reflectivity of a high-index semiconductor such as Germanium (40%).

The small difference in the center frequency of the etalons described above (so that they overlap the absorption line) can most easily be obtained by splitting the incident light into two paths and sending the two paths through the same etalon (i.e., optical element) at two slightly different angles. The optimal etalon frequency offset is chosen by balancing the high relative sensitivity obtained by a small frequency offset shown in FIG. 14A against the increased capability of measuring the laser frequency noise afforded by an increased frequency offset. A good choice for the etalon frequency offset is about 40% of the gas absorption linewidth, or ±400 MHz (800 MHz total) in the example above. This frequency separation can be provided by setting the angle of the two beams incident on the etalon differently, which then modifies the effective thickness (FSR) of the etalon slightly. This has the advantage that the free spectral range is effectively the same (it varies slowly with angle) and there is no non-common drift: there is only one physical optical element. The frequency offset with angle tuning of an etalon is given by Eq. 10 below, where n is the index of refraction of the etalon (4.2 for Ge, 1 for air gap), v is the light frequency, and θ is the etalon (external) angle of incidence.

$$\delta v \cong v\left(1 - \cos\frac{\theta}{n}\right) \quad (10)$$

For an air gap etalon, a frequency separation of 800 MHz (+/−400 MHz) corresponds to an angle offset of approximately 0.2 degrees, but as the etalon response is periodic, values which shift by the desired amount+n*FSR, where n is a small integer, will work. For example, a total shift of 60 GHz+800 MHz (that is, three times the 20-GHz FSR described above plus the offset) indicates that an angle offset between the two beams of about 2 degrees with an air gap etalon is suitable.

Most simple methods of generating two distinct angles of etalon incidence will tend to cause the two beams to hit slightly different regions of the etalon—this introduces a problem: the etalon FSR is a function of temperature (as it expands/contracts the structure), and, as the FSR shifts, the absolute frequency of the maxima of transmission move around rapidly.

Etalon transmission frequency shifts with temperature can range from 8 GHz/° C. for germanium, or 6 GHz/° C. for silicon, to 2 MHz/° C. for air gap etalons. For the DUET method to work without temperature stability being a significant noise source, the two effective etalon transmission maxima must retain their set offset to within about 10% of the absorption linewidth of the species of interest. In addition to absolute stability of this order, the temperature differential in the structure between the two spots must be maintained to this level of accuracy, otherwise the detector will exhibit noise corresponding to thermal gradients within the etalon.

EXEMPLIFICATION

Using the optimal etalon design determined using parametric studies as previously described above, a fieldable prototype DUET receiver, schematically illustrated in FIG. 5A, was fabricated. Important design choices were the choice of etalon, the method of generating the offset angle between the two beams, and the method of collecting the light reflected off the etalon.

Etalon Design

When choosing the etalon, thermal stability requirements set the choice of material. Thermal stability of better than ±0.02° C. would have been required for silicon and germanium solid etalons, while stability of approximately ±25° C. was required for an air gap etalon. As temperature stabilization better than 0.1° C. is quite challenging, and having as few active components as possible were desired, an air gap-based etalon was chosen.

The use of an air-gap etalon placed wavelength restrictions on the final design. An air gap etalon requires two different kinds of dielectric coating types (anti-reflection (AR) on the outside surfaces, and the design reflectivity on the inside), and the ability to manufacture these coatings so that they meet the required reflectivity over a large wavelength range determines the operating wavelength bandwidth of the receiver. In an air gap etalon, the two exterior surfaces are AR coated, and the two interior surfaces coated to give the desired etalon finesse (60%, for example). For the DUET method to work, the reflections off the exterior faces must be negligible; the system cannot compensate or correct for light that doesn't interact with the actual resonant cavity. To achieve negligible reflection, AR coatings with reflectivity of <0.1% are required. AR coatings with that stringent specification can be designed to work at a specific wavelength, but not over a large range; the range over which the AR coated surface reflectivity is <0.1% is the frequency range over which a particular etalon would work (the prototype system meets the above specifications over about 40 nm of bandwidth).

Solid etalons, such as one fabricated from silicon or fused silica, would not require the AR coating, as there are only two optical surfaces, both with the finesse-determined reflectivity. Optical coatings with reflectivity of about 50% can be produced that work over very large frequency excursions, thus a solid etalon can be designed which will function over, for example, the entire tuning range of a representative tunable laser system (2.2-3.8 µm), at the cost of requiring etalon temperature stabilization, and with some variability of absolute sensitivity due to imprecise reflectivities over large wavelength ranges.

Offset Angle

As the desired etalon frequency offset of ±400 MHz could be achieved using a relative deflection angle offset between the two beams of about 2°, it is possible to use a commercial Wollaston prism polarizer to produce the two beams. A Wollaston prism polarizer consists of two right angle prisms made of a birefringent crystal, bonded together, with their optical axes orthogonal to each other. A single beam of mixed polarization will split into two orthogonally polarized beams propagating at a small angle (about ±1° to the incident light path. It is also possible to slightly tune the relative angle between these two beams by rotating the polarizer relative to the incident beam (a 10° rotation of the polarizer produces a ~0.05° change in the output beam separation). This ability to finely adjust the beam angle allows the precise tuning of etalon frequency offset after system assembly.

The particular Wollaston prism used was a 30 mm clear aperture, nominal 2° separation quartz polarizer. Its angle was adjustable by ±10 degrees in the plane of the detector, which, when coupled with the particular etalon chosen, allowed the tuning of etalon offset from 0-2 GHz.

Reflected Beam Collection

As the beam internal to the optical system was nominally 20 mm in diameter, using an angled etalon to allow the collection of its reflected beam was impractical. The cosine dependence of the offset tuning shows that one wants to be as close to normal as possible, to prevent the system from tuning too quickly (and therefore being more sensitive to changes in pointing angle). The maximum etalon angle to keep the angle sensitivity reasonable is approximately 5°, and for two large beams to be separated, this would require at least 0.5 m of optical path. With optical paths that long, clipping, beam collimation and divergence, and scattered light all present challenges. At the cost of overall receiver loss, a 50:50 non-polarizing beamsplitter was used to collect the reflected light and send it to a detector assembly. This actually results in a total power loss of 4.8 dB (rather than 6 dB, because the etalon reflectivity can be adjusted to send more light into the reflected channel), but the design maintains relatively small size, common path optics, and removes requirements on exact etalon angle.

The tunable source is a pulsed MWIR source, which is tunable from 2.2-3.8 microns, and has about 1.4 GHz of bandwidth. When actively stabilized, the system has frequency stability to better than 5 MHz RMS, and when not actively stabilized a frequency stability of 400 MHz. It is capable of switching between two different lines approximately 10 GHz apart, permitting 2-color DIAL measurements.

Figure 15:
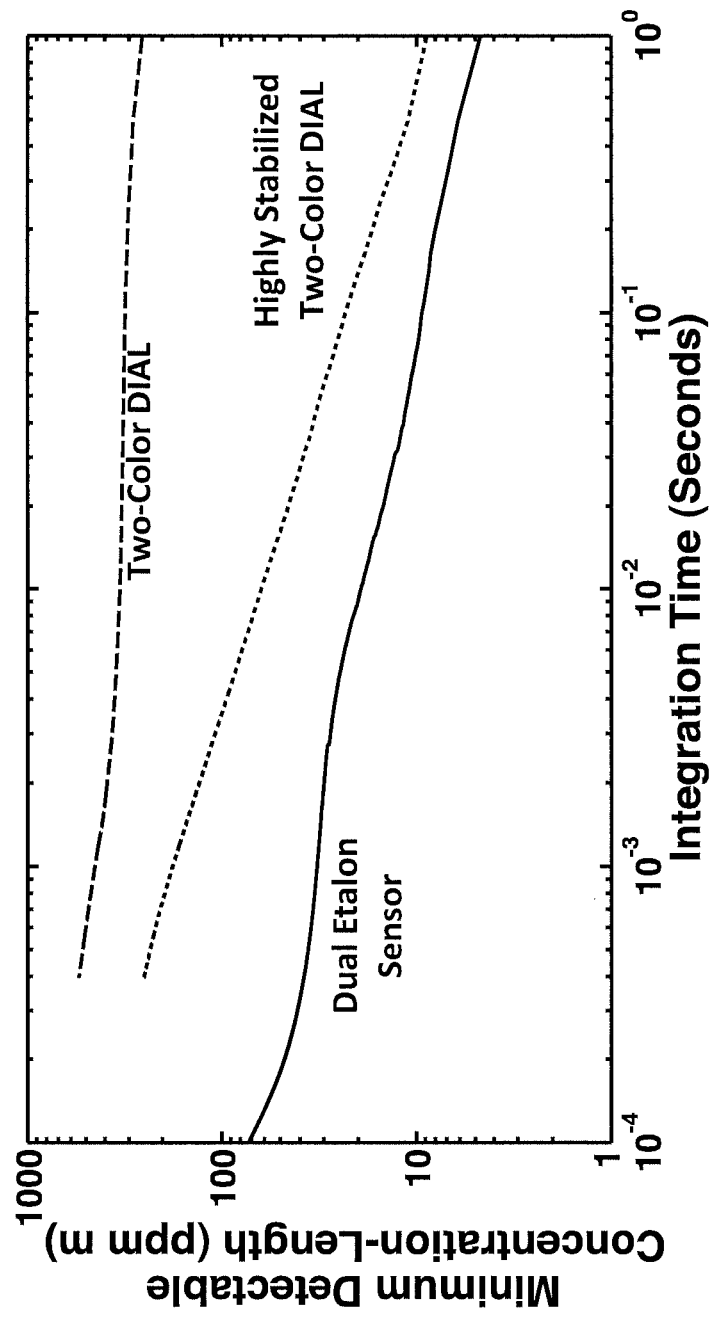
FIG. 15 is a graph of the minimum detectable concentration-length as a function of integration time, showing the DUET CO detection performance using the MWIR source described herein. The system response is shown both utilizing the DUET method, and acting as a traditional 2-color DIAL system. DUET sensitivity for a source with frequency stability noise of 400 MHz is improved by about 40 times over that of traditional DIAL with a 1 second integration time. Performance of DUET is also better than that of traditional DIAL using a source actively frequency stabilized to <5 MHz. Sensitivity of DUET to CO over a 1.6 km propagation distance was shown to be 5 ppm·m/rt. Hz.

To test DUET performance at a significant range, the system was tuned onto the 2.35 µm line of carbon monoxide (CO), and then propagated outdoors over a one-way path of 1.6 km. For measuring the baseline system performance as a canonical 2-color DIAL detector, the source was operated in both the actively stabilized and non-actively stabilized states, and performance measured with varying integration times, as shown in FIG. 15. Additionally, the DUET receiver was used with the source in the non-actively stabilized single-color state, and its performance is shown in FIG. 15.

While this invention has been particularly shown and described with references to example embodiments thereof, it will be understood by those skilled in the art that various changes in form and details may be made therein without departing from the scope of the invention encompassed by the appended claims.

What is claimed is:
1. A gas detector comprising:
a receiver configured to receive light from a light source through gas, the light source having a bandwidth on the order of an absorption linewidth of the gas, the absorption linewidth of the gas being in a range of between about 1 GHz and about 5 GHz, and the receiver including at least a first etalon having a transmission bandwidth on the order of the absorption linewidth of the gas, the transmission bandwidth of the first etalon being substantially smaller than the bandwidth of the light source;

a first detector for detecting light transmitted through the first etalon;

a second detector for detecting light reflected from the first etalon; and a processor that determines the quantity of gas based on the detected transmitted and reflected light.

2. The gas detector of claim 1, further including a light source having an optical bandwidth on the order of the absorption linewidth of the gas.

3. The gas detector of claim 2, wherein the bandwidth of the light source is in a range of between about 0.3 times the absorption linewidth of the gas and about seven times the absorption linewidth of the gas.

4. The gas detector of claim 2, wherein the bandwidth of the light source is in a range of between approximating the absorption linewidth of the gas and about three times the absorption linewidth of the gas.

5. The gas detector of claim 1, wherein the transmission bandwidth of the first etalon is in a range of between approximating the absorption linewidth of the gas and about four times the absorption linewidth.

6. The gas detector of claim 1, wherein the transmission bandwidth of the first etalon is in a range of between approximating the absorption linewidth of the gas and about two times the absorption linewidth.

7. The gas detector of claim 1, wherein the transmission bandwidth of the first etalon is in a range of between about 10% and about 250% of the bandwidth of the light source.

8. The gas detector of claim 1, wherein the transmission bandwidth of the first etalon is in a range of between about 25% and about 75% of the bandwidth of the light source.

9. The gas detector of claim 1, wherein the processor calculates a ratio of reflected light to transmitted light in determining the quantity of gas.

10. A method of detecting a gas comprising:
receiving light from a light source through gas, the light source having an optical bandwidth on the order of an absorption linewidth of the gas, the absorption linewidth of the gas being in a range of between about 1 GHz and about 5 GHz;
directing the light to at least a first etalon having a transmission bandwidth on the order of the absorption linewidth of the gas, the transmission bandwidth of the first etalon being substantially smaller than the bandwidth of the light source;
detecting light transmitted through the first etalon;
detecting light reflected from the first etalon; and
determining the quantity of gas based on the detected signals.

11. The method of claim 10, wherein the bandwidth of the light source is in a range of between about 0.3 times the absorption linewidth of the gas and about seven times the absorption linewidth of the gas.

12. The method of claim 10, wherein the bandwidth of the light source is in a range of between approximating the absorption linewidth of the gas and about three times the absorption linewidth of the gas.

13. The method of claim 10, wherein determining the quantity of gas includes calculating a ratio of reflected light to transmitted light.

14. The method of claim 10, wherein the transmission bandwidth of the first etalon is in a range of between approximating the absorption linewidth of the gas and about four times the absorption linewidth.

15. The method of claim 10, wherein the transmission bandwidth of the first etalon is in a range of between approximating the absorption linewidth of the gas and about two times the absorption linewidth.

16. The method of claim 10, wherein the transmission bandwidth of the first etalon is in a range of between about 10% and about 250% of the bandwidth of the light source.

17. The method of claim 10, wherein the transmission bandwidth of the first etalon is in a range of between about 25% and about 75% of the bandwidth of the light source.

18. A method of detecting a gas comprising:
receiving light from a light source through gas, the light source having an optical bandwidth on the order of an absorption linewidth of the gas, the absorption linewidth of the gas being in a range of between about 1 GHz and about 5 GHz;
detecting a first portion of the light source bandwidth that coincides with at least a portion of the gas absorption linewidth;
detecting a first remaining portion of the light source bandwidth;
detecting an adjacent portion of the light source bandwidth that coincides with at least a portion of the gas absorption linewidth;
detecting a second remaining portion of the light source bandwidth; and
determining the quantity of gas based on the detected signals.

19. The method of claim 18, wherein the bandwidth of the light source is in a range of between about 0.3 times the absorption linewidth of the gas and about seven times the absorption linewidth of the gas.

20. The method of claim 18, wherein the bandwidth of the light source is in a range of between approximating the absorption linewidth of the gas and about three times the absorption linewidth of the gas.

21. A gas detector comprising:
a receiver configured to receive light from a light source through gas, the light source having a bandwidth on the order of an absorption linewidth of the gas, the receiver including at least:
a first etalon having a transmission bandwidth on the order of the absorption linewidth of the gas, the transmission bandwidth of the first etalon being substantially smaller than the bandwidth of the light source;
a beam splitter that separates the light from the light source into a first beam directed to the first etalon and a second beam;
a second etalon configured to receive the second beam and having a transmission bandwidth on the order of the absorption linewidth of the gas, the transmission bandwidth of the second etalon being approximately equal and adjacent to the transmission bandwidth of the first etalon, the transmission bandwidths of the first and second etalons each overlapping the absorption bandwidth of the gas and being substantially smaller than the bandwidth of the light source;
a first detector for detecting light transmitted through the first etalon;
a second detector for detecting light reflected from the first etalon;
a third detector for detecting light transmitted through the second etalon; and
a fourth detector for detecting light reflected from the second etalon;

a processor that determines the quantity of gas based on the detected transmitted and reflected light at the first and second etalon.

22. The gas detector of claim 21, wherein the transmission bandwidth of the second etalon is in a range of between approximating the absorption linewidth of the gas and about four times the absorption linewidth.

23. The gas detector of claim 21, wherein the transmission bandwidth of the second etalon is in a range of between approximating the absorption linewidth of the gas and about two times the absorption linewidth.

24. The gas detector of claim 21, wherein the transmission bandwidth of the second etalon is in a range of between about 10% and about 250% of the bandwidth of the light source.

25. The gas detector of claim 21, wherein the transmission bandwidth of the second etalon is in a range of between about 25% and about 75% of the bandwidth of the light source.

26. The gas detector of claim 21, wherein the processor calculates the sum of ratios of reflected light to transmitted light at the first and second etalon in determining the quantity of gas.

27. A gas detector comprising:
a receiver configured to receive light from a light source through gas, the light source having a bandwidth on the order of an absorption linewidth of the gas, the receiver including at least:
an etalon having a transmission bandwidth on the order of the absorption linewidth of the gas, the transmission bandwidth of the etalon being substantially smaller than the bandwidth of the light source;
a beam separator that separates the light from the light source into a first beam and a second beam, with a small deflection angle between the first beam and the second beam;
a first detector for detecting light from the first beam transmitted through the etalon;
a second detector for detecting light from the first beam reflected from the etalon;
a third detector for detecting light from the second beam transmitted through the etalon; and
a fourth detector for detecting light from the second beam reflected from the etalon; and
a processor that determines the quantity of gas based on the transmitted and reflected light.

28. The gas detector of claim 27, wherein the beam separator includes a beam splitter.

29. The gas detector of claim 27, wherein the beam separator includes a birefringent wedge.

30. The gas detector of claim 27, wherein the deflection angle is in a range of between about 0.25 degrees and about five degrees.

31. A method of detecting a gas comprising:
receiving light from a light source through gas, the light source having an optical bandwidth on the order of an absorption linewidth of the gas;
directing the light to at least a first etalon having a transmission bandwidth on the order of the absorption linewidth of the gas, the transmission bandwidth of the first etalon being substantially smaller than the bandwidth of the light source;
separating the light from the light source into a first beam directed to the first etalon and a second beam;
receiving the second beam at a second etalon having a transmission bandwidth on the order of the absorption linewidth of the gas, the transmission bandwidth of the second etalon being approximately equal and adjacent to the transmission bandwidth of the first etalon, wherein the transmission bandwidths of the first and second etalon each overlap the absorption bandwidth of the gas and are substantially smaller than the bandwidth of the light source;
detecting light transmitted through the first etalon;
detecting light reflected from the first etalon;
detecting light transmitted through the second etalon;
detecting light reflected from the second etalon; and
determining the quantity of gas based on the detected signals.

32. The method of claim 31, wherein determining the quantity of gas includes calculating the sum of ratios of reflected light to transmitted light at the first and second etalon.

33. The method of claim 31, wherein the transmission bandwidth of the second etalon is in a range of between approximating the absorption linewidth of the gas and about four times the absorption linewidth.

34. The method of claim 33, wherein the transmission bandwidth of the second etalon is in a range of between approximating the absorption linewidth of the gas and about two times the absorption linewidth.

35. The method of claim 31, wherein the transmission bandwidth of the second etalon is in a range of between about 10% and about 250% of the bandwidth of the light source.

36. The method of claim 31, wherein the transmission bandwidth of the second etalon is in a range of between about 25% and about 75% of the bandwidth of the light source.

37. A method of detecting a gas comprising:
receiving light from a light source through gas, the light source having an optical bandwidth on the order of an absorption linewidth of the gas;
separating the light from the light source into a first beam and a second beam, with a small deflection angle between the first beam and the second beam;
directing the first beam and the second beam to an etalon having a transmission bandwidth on the order of the absorption linewidth of the gas, the transmission bandwidth of the etalon being substantially smaller than the bandwidth of the light source;
detecting light from the first beam transmitted through the etalon;
detecting light from the first beam reflected from the etalon;
detecting light from the second beam transmitted through the etalon;
detecting light from the second beam reflected from the etalon; and
determining the quantity of gas based on the detected signals.

38. The method of claim 37, wherein the deflection angle is in a range of between about 0.25 degrees and about five degrees.

39. A method of detecting a gas comprising:
receiving light from a light source through gas, the light source having an optical bandwidth on the order of an absorption linewidth of the gas,
detecting a first portion of the light source bandwidth that coincides with at least a portion of the gas absorption linewidth;
directing the first portion of the light source bandwidth to a first etalon having a transmission bandwidth on the order of the absorption linewidth of the gas, the transmission bandwidth of the first etalon being substantially smaller than the bandwidth of the light source
detecting a first remaining portion of the light source bandwidth;

detecting an adjacent portion of the light source bandwidth that coincides with at least a portion of the gas absorption linewidth;

detecting a second remaining portion of the light source bandwidth;

directing the second remaining portion of the light source bandwidth to a second etalon having a transmission bandwidth on the order of the absorption linewidth of the gas, the transmission bandwidth of the second etalon being approximately equal and adjacent to the transmission bandwidth of the first etalon, wherein the transmission bandwidths of the first and second etalon each overlap the absorption bandwidth of the gas and are substantially smaller than the bandwidth of the light source; and determining the quantity of gas based on the detected signals.

* * * * *